United States Patent [19]

Holick et al.

[11] Patent Number: 4,636,566

[45] Date of Patent: Jan. 13, 1987

[54] PROCESS FOR PREPARING D-(+)-BIOTIN AND INTERMEDIATES THEREFOR

[75] Inventors: Wolfgang Holick, Grenzach-Wyhlen, Fed. Rep. of Germany; Horst Pauling, Bottmingen, Switzerland

[73] Assignee: Hoffmann-La Roche Inc., Nutley, N.J.

[21] Appl. No.: 705,775

[22] Filed: Feb. 26, 1985

[30] Foreign Application Priority Data

Mar. 9, 1984 [CH] Switzerland ............... 1171/84

[51] Int. Cl.$^4$ ............................. C07D 495/04
[52] U.S. Cl. ................................. 548/303
[58] Field of Search ........................ 548/303

[56] References Cited

U.S. PATENT DOCUMENTS 2,489,232  11/1949  Goldberg et al. ............ 548/303

FOREIGN PATENT DOCUMENTS 84377    7/1983  European Pat. Off. ......... 548/303
1320799  6/1973  United Kingdom ............. 548/303

OTHER PUBLICATIONS

Stetter, H. et al., Chem. Ber. 85, 451 (1952).
Stetter, H. et al., Chem. Ber. 86, 790 (1953).
Stetter, H. et al., Chem. Ber. 87, 205 (1954).
Voss, G. et al., Helv. Chim. Acta. 66, 2294 (1983).

Primary Examiner—Richard A. Schwartz
Assistant Examiner—Kurt G. Briscoe
Attorney, Agent, or Firm—Jon S. Saxe; Bernard S. Leon; Matthew Boxer

[57] ABSTRACT

A process for the manufacture of intermediates in the synthesis of biotin as well as of biotin itself is described. In this process the side chain is attached to the ring system by means of a Grignard reaction, the resulting compound is then dehydrated and subsequently reduced.

3 Claims, No Drawings

PROCESS FOR PREPARING D-(+)-BIOTIN AND INTERMEDIATES THEREFOR

BACKGROUND OF THE INVENTION

1. Field of the Invention

The present invention is concerned with a novel process for the manufacture of heterocyclic compounds, which are suitable as intermediates for the manufacture of D-(+)-biotin, as well as a process for the manufacture of D-(+)-biotin itself. The invention is also concerned with novel intermediates in this process.

2. Background Description

D-(+)-Biotin is a substance which has been known for a long time and a number of processes for its manufacture are also already known. The necessity of attaching the carboxybutyl side chain to the ring system at some stage is common to the technically interesting processes. Various solutions are known for this such as, for example, the synthesis of the side chain according to the coupling scheme $C_4+C_1 \rightarrow C_5$ or also $C_3+(C_3-C_1=C_2)\rightarrow C_5$. It is also known to attach the side chain to the ring system in one step by means of a Wittig reaction. However, all of these processes have the disadvantage that they either proceed via a relatively large number of reaction steps or require a relatively large expenditure for the isolation of the desired end product.

There accordingly exists a need for a technically simple process in which the side chain can be attached to the ring system in good yield and in as far as possible one reaction step. This is now possible by means of the process of the invention.

SUMMARY OF THE INVENTION

The present invention concerns a process comprising reacting the thiolactone of the formula:

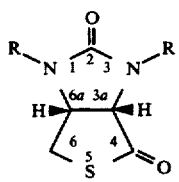

wherein
R represents the benzyl group, with a Grignard compound of the formula:

   II wherein
X represents halogen and $R^1$ signifies the residue of the formula:

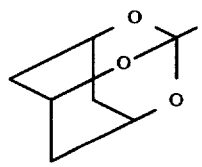

and, if desired, dehydrating the thus-obtained compound of the formula:

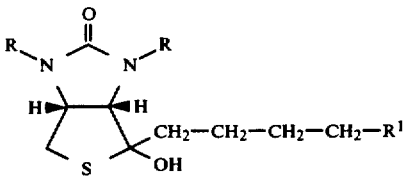   III wherein
R and $R^1$ have the above significance, if desired, liberating the carboxyl group in the side chain in the thus-obtained compound of the formula:

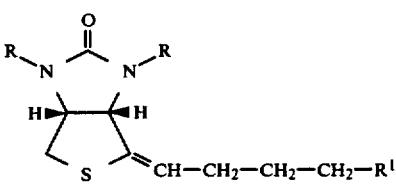   IV wherein
R and $R^1$ have the above significance, by the cleavage of cis-1,3,5-cyclohexanetriol, and, if desired, converting the thus-obtained compound of the formula:

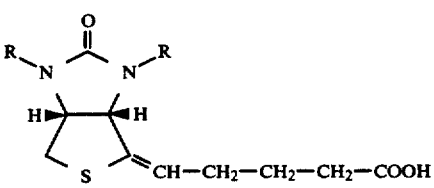   V wherein
R has the above significance, into D-(+)-biotin.

DETAILED DESCRIPTION OF THE INVENTION

The present invention concerns the process of reacting a thiolactone of the formula:

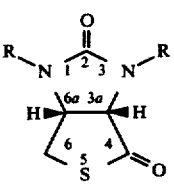   I wherein
R is benzyl, with a Grignard compound of the formula:

   II wherein
X is halogen and $R^1$ is a residue of the formula:

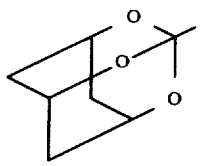

to form a compound of the formula:

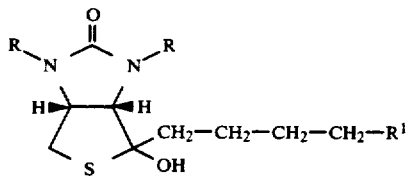

III wherein

R and R[1] are as above. If desired, the compound of formula III may be dehydrated to yield a compound of the formula:

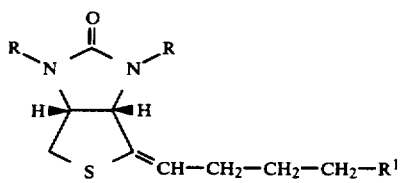

IV wherein

R and R[1] are the same as above. If desired, the carboxyl group in the side chain of compound IV may be liberated by cleaving cis-1,3,5-cyclohexanetriol, to form a compound of the formula:

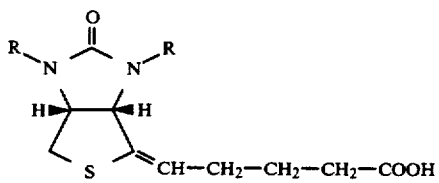

V wherein

R is the same as above.

If desired, the compound V may then be converted into D-(+)-biotin.

The term "halogen" as used throughout the specification signifies chlorine, bromine and iodine. Bromine is the preferred halogen.

The compounds of formulae I and II, used as the starting materials, as well as the compound of formula V, manufactured in accordance with the invention, are known compounds. The compounds of formulae III and IV are, however, novel and are likewise objects of the present invention.

The reaction of the thiolactone of formula I with a Grignard compound of formula II can be carried out in a manner known per se, i.e. under the conditions which are usual for a Grignard reaction. This reaction is conveniently carried out in an organic solvent which is inert under the reaction conditions, for example in a lower alkyl ether such as diethyl ether or a cyclic ether such as tetrahydrofuran, dioxan and the like and at a temperature of about −20° C. to the boiling point of the solvent used, preferably at about 0° C. to about 50° C., and more preferably at room temperature.

The dehydration of the compound of formula III can be carried out in a manner known per se. This dehydration is conveniently carried out by treatment with an acid such as, for example, sulphuric acid, hydrochloric acid, p-toluene-sulphonic acid and the like. As the solvent there is conveniently used one which forms an azeotrope with the water which is formed, e.g. aromatic hydrocarbons such as benzene, toluene, xylene and the like. The dehydration is also advantageously carried out at an elevated temperature, preferably at the reflux temperature of the reaction mixture.

The cleavage of the cis-1,3,5-cyclohexanetriol from the compound of formula IV, i.e. the liberation of the carboxyl group at the C$_4$-atom of the side chain, can be carried out in a manner known per se. This cleavage can be carried out conveniently by treatment with an aqueous mineral acid such as sulphuric acid, hydrobromic acid, hydrochloric acid and the like, this reaction being accelerated by the addition of catalytic amounts of p-toluenesulphonic acid. In order to complete the reaction, the reaction mixture is subsequently heated under reflux with aqueous alkali hydroxide solution. As the alkali hydroxide there can be named here lithium hydroxide, potassium hydroxide and sodium hydroxide.

The dehydration of the compound of formula III to the compound of formula IV and the subsequent cleavage of the cis-1,3,5-cyclohexanetriol can be carried out not only in a one-pot process, but also in two separate steps with the intermediate isolation of the compound of formula IV.

The compound of formula V obtained after the cleavage of the cis-1,3,5-cyclohexanetriol is, as already mentioned, a known compound and can be converted readily into D-(+)-biotin in a known manner, i.e. by hydrogenation of the double bond and cleavage of the protecting groups on the nitrogen atoms.

The following Examples illustrate the inventive process. Unless otherwise stated, percentages and ratios relating to solvent mixtures are expressed in volume, purity data determined by gas chromatography are expressed in area % and the remaining percentages and ratios are expressed in weight. Temperatures are in degrees Celsius (°C.), normal pressure is about 1 atmosphere and room temperature is about 23° C. Unless indicated otherwise, the Examples were carried out as written.

EXAMPLE 1

1.35 g (4.5 mmol) of 4-(2,4,10-trioxaadamantyl)-butyl-magnesium bromide in 45 ml of tetrahydrofuran are slowly added dropwise at room temperature under argon to a solution of 1.52 g (4.5 mmol) of (+)-cis-1,3-dibenzyl-hexahydro-1H-thieno[3,4-d]imidazole-2,4-dione in 25 ml of tetrahydrofuran. The mixture is stirred at room temperature for a further 15 hours, then diluted with 300 ml of ethyl acetate and treated with 100 ml of 1N hydrochloric acid. The organic phase is separated, washed with 10 wt.% bicarbonate solution, with water and with saturated sodium chloride solution and dried over sodium sulphate. The residue remaining after removing the solvent is chromatographed on silica gel. Elution with toluene, toluene/ethyl acetate (2:1) and toluene/ethyl acetate (1:2) gives firstly 0.5 g of a white, waxy mass. There are subsequently eluted 1.75 g (73% of theory) of cis-1,3-dibenzyl-4-hydroxy-4-(4-(2,4,10-trioxaadamantyl)-butyl)-hexahydro-1H-thieno[3,4-d]imidazol-2-one in the form of a white powder. Melting point 186°-192° C.

EXAMPLE 2

1.61 g (3 mmol) of cis-1,3-dibenzyl-4-hydroxy-4-(4-(2,4,10-trioxaadamantyl)-butyl)-hexahydro-1H-thieno[3,4-d]imidazol-2-one (prepared in accordance with Example 1) are dissolved in 50 ml of toluene, the solution is treated with 5 mg of p-toluenesulphonic acid and heated to boiling. 20 ml of toluene are distilled off within 30 minutes. After this time starting material can no longer be detected in a thin-layer chromatogram. The solution is now evaporated to dryness. The residue is taken up with 8.5 ml of dioxan, the solution is treated with 8.5 ml of 0.02N sulphuric acid and boiled under reflux for 2 hours. Thereafter, the mixture is made alkaline with 2.85 ml of 2N sodium hydroxide solution and boiled under reflux for a further 30 minutes. The mixture is subsequently cooled to room temperature and acidified with dilute hydrochloric acid. The solution is then extracted with a total of 200 ml of ethyl acetate. The combined extracts are washed with water and saturated sodium chloride solution and dried over sodium sulphate. The residue remaining after removing the solvent is chromatographed on silica gel. Elution with toluene, toluene/ethyl acetate (9:1), (8:2), (1:1) and with pure ethyl acetate gives 955 mg (76% of theory) of cis-2-oxo-1,3-dibenzyl-hexahydro-1H-thieno[3,4-d]imidazol-4-ylidenepentanoic acid as a light brown oil which solidifies under drying.

$^1$H-NMR (80 MHz, CDCl$_3$): 1.4–1.9 ppm (m) and 1.9–2.5 ppm (m), 6H, 2.96 ppm (d) 2H, 3.8–4.4 ppm (m) and 4H, 4.82 ppm (d) and 4.95 ppm (d) 2H, 5.43 ppm (t) 1H, 7.3 ppm (m) 10H, 8.5 ppm (broad) 1H.

IR: 703, 754, 1181, 1234, 1495, 1583, 1657, 1696, 1732 cm$^{-1}$.

MS: M=422.

EXAMPLE 3

910 mg (1.68 mmol) of cis-1,3-dibenzyl-4-hydroxy-4-(4-(2,4,10-trioxaadamantyl)-butyl)-hexahydro-1H-thieno[3,4-d]imidazol-2-one (prepared in accordance with Example 1) are dissolved in 50 ml of toluene and the solution is treated with 20 mg of p-toluenesulphonic acid. The solution is heated to boiling and 20 ml of toluene are distilled off within 1 hour. Thereafter, the solution is evaporated to dryness. The residue remaining is chromatographed on silica gel. Elution with toluene, toluene/ethyl acetate (9:1) and (8:2) gives 839 mg (96% of theory) of cis-1,3-dibenzyl-4-(4-(2,4,10-trioxaadamantyl)-butylidene)-hexahydro-1H-thieno[3,4-d]imidazol-2-one in the form of a light brown oil which solidifies upon drying.

$^1$H-NMR (80 MHz, CDCl$_3$): 1.2–2.3 ppm (m) and 2.3–2.8 ppm (m) 12H, 2.95 ppm (d) 2H, 3.8–4.5 ppm (m) 7H, 4.79 ppm (d) and 4.96 ppm (d) 2H, 5.45 ppm (t) 1H, 7.38 ppm (m) 10H.

EXAMPLE 4

839 mg (1.62 mmol) of cis-1,3-dibenzyl-4-(4-(2,4,10-trioxaadamantyl)-butylidene)-hexahydro-1H-thieno[3,4-d]imidazol-2-one (prepared in accordance with Example 3) are treated with 4.6 ml of dioxan, 4.6 ml of 0.2N sulphuric acid as well as 20 mg of p-toluenesulphonic acid and the mixture is heated to boiling under an argon atmosphere for 2.5 hours. The mixture is subsequently made alkaline with 1.54 ml of 2N sodium hydroxide solution and boiled under reflux for a further 45 minutes. After cooling to room temperature the solution is extracted with ethyl acetate and the extract is discarded. The aqueous phase is acidified with dilute hydrochloric acid and again extracted with a total of 200 ml of ethyl acetate. The combined extracts are washed once with saturated sodium chloride solution and dried over sodium sulphate. After removing the solvent there are obtained 622 mg (89% of theory) of cis-2-oxo-1,3-dibenzyl-hexahydro-1H-thieno[3,4-d]imidazol-4-ylidenepentanoic acid.

We claim:

1. A process for manufacturing D-(+)-biotin which process comprises reacting a thiolactone of the formula:

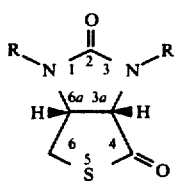

wherein
R is benzyl, with a Grignard compound of the formula:

II
wherein X is halogen, and R$^1$ is

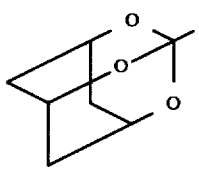

to obtain a compound of the formula

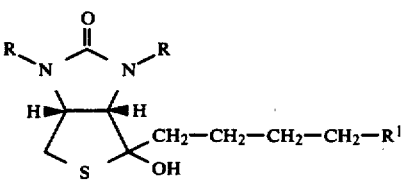

III wherein
R and R$^1$ are as above and dehydrating the compound of formula III to form a compound of the formula:

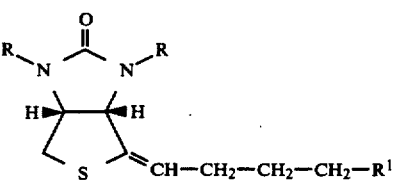

IV wherein
R and R$^1$ are as above and cleaving cis-1,3,5-cyclohexanetriol from the compound of formula IV to form the compound of the formula:

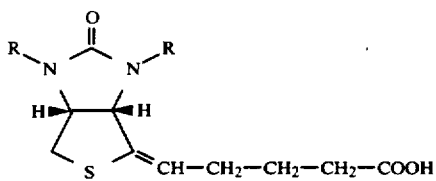
wherein
R is as above and converting the compound of formula V to D-(+)-biotin by hydrogenation of the double bond and cleavage of the protecting groups on the nitrogen atoms.
2. A comound of the formula
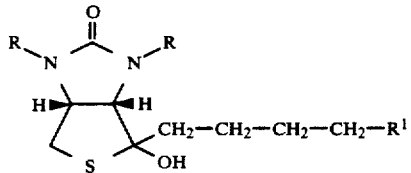
wherein
R is benzyl and R¹ is a residue of the formula:
V
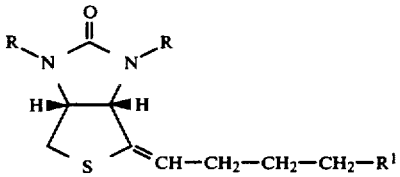
3. A compound of the formula:
IV
wherein
R is benzyl and R¹ is a residue of the formula:
* * * * *

UNITED STATES PATENT AND TRADEMARK OFFICE
CERTIFICATE OF CORRECTION

PATENT NO. : 4,636,566

DATED : January 13, 1987

INVENTOR(S) : Wolfgang Holick and Horst Pauling

It is certified that error appears in the above-identified patent and that said Letters Patent is hereby corrected as shown below:

In claim 2, line 1, delete "comound" and insert therefor -- compound --.

Signed and Sealed this

Twenty-eighth Day of June, 1988

Attest:

DONALD J. QUIGG

Attesting Officer          Commissioner of Patents and Trademarks